United States Patent [19]
Hashizume et al.

[11] Patent Number: 5,932,755
[45] Date of Patent: Aug. 3, 1999

[54] FATTY ACID ESTER OF ETHERIFIED POLYHYDRIC ALCOHOL

[75] Inventors: Naomichi Hashizume; Hiroshi Kamitani, both of Wakayama; Katsumi Kita, Izumisano, all of Japan

[73] Assignee: Kao Corporation, Tokyo, Japan

[21] Appl. No.: 08/750,473

[22] PCT Filed: Jun. 7, 1995

[86] PCT No.: PCT/JP95/01142

§ 371 Date: Dec. 16, 1996

§ 102(e) Date: Dec. 16, 1996

[87] PCT Pub. No.: WO95/34527

PCT Pub. Date: Dec. 21, 1995

[30] Foreign Application Priority Data

Jun. 16, 1994 [JP] Japan .................................... 6-134066
Jun. 16, 1994 [JP] Japan .................................... 6-134067

[51] Int. Cl.[6] .................................................. C07C 53/00
[52] U.S. Cl. ............................ 554/227; 424/401; 424/63
[58] Field of Search ........................... 554/227; 424/401; 426/63

[56] References Cited

U.S. PATENT DOCUMENTS 5,429,820 7/1995 Kamitani ................................ 424/401

FOREIGN PATENT DOCUMENTS 0 512 270 11/1992 European Pat. Off. .
4-190358 7/1992 Japan .
5-92910 4/1993 Japan .

OTHER PUBLICATIONS

Chemical Abtsr., vol. 124, abstr. #89978, 1995.

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

The present invention relates to a fatty acid ester of an etherified polyhydric alcohol represented by the following general formula (1), a production process thereof, a cosmetic composition comprising this compound, and a production process of an etherified polyhydric alcohol via the ester.

$$G(A)_x(B)_y \qquad (1)$$

(G: a residue formed by removing H atoms of all the OH groups of a polyhydric alcohol having at least three OH groups, A: —$CH_2CH(OH)R$ or —$CHRCH_2OH$, $R^1$: $R^{1a}$ or —$CH_2OR^{1a}$ ($R^{1a}$: $C_1$–$C_{36}$ alkyl or alkenyl group), B: H or $C_1$–$C_{11}$ acyl group, x+y: the number of the OH groups of G, $x \geq 1$, $y \geq 1$, and at least one of y groups B: alkanoyl group).

The compound (1) is not only useful as an intermediate for the production of an etherified polyhydric alcohol, but also excellent per se in the performance as a cosmetic base, emulsifier, lubricant, oily component and the like.

28 Claims, No Drawings

FATTY ACID ESTER OF ETHERIFIED POLYHYDRIC ALCOHOL

This is the U.S. National Stage Application of PCT/JP95/01142 filed Jun. 7, 1995 now WO95/34527 published Dec. 21, 1995.

TECHNICAL FIELD

The present invention relates to a fatty acid ester of an etherified polyhydric alcohol, which is useful per se as a base, emulsifier, lubricant, oily component and the like for cosmetic compositions and the like, and is also useful as an intermediate for the production of a glyceryl-etherified polyhydric alcohol or hydroxyalkyl-etherified polyhydric alcohol which is used for the same purposes as mentioned above, and to a production process thereof.

BACKGROUND ART

Polyol ethers such as polyoxyalkylene alkyl ethers and polyoxyalkylene ethers of sorbitan esters, and alkyl-etherified polyhydric alcohols have heretofore been used as bases, emulsifiers, lubricants, oily components and the like for perfumed toiletries and cosmetics.

Of these compounds, the polyol ethers have been produced by the addition reaction of an alkylene oxide such as ethylene oxide or propylene oxide. However, the resultant products are obtained in the form of a mixture of those having various polyalkylene chain lengths, and it has been difficult to synthesize these products in a high purity form. Such products have not attained satisfactory performance in some cases when used for the purposes of cosmetics, perfumed toiletries and the like. On the other hand, those having good properties have existed in a part of the alkyl-etherified polyhydric alcohols (glyceryl-etherified polyhydric alcohols and hydroxyalkyl-etherified polyhydric alcohols, Japanese Patent Application Laid-Open No. 984/1993). However, many of them have involved such a problem that they are solids having a high melting point, that they are difficult to homogeneously disperse in water because of the mismached allocation balance of both substituents, a hydrophilic group and a lipophilic group, and that they have no good affinity with any solvents of various kinds.

There has thus been a demand for development of a compound which is excellent in the performance as a base, emulsifier, lubricant, oily component and the like for cosmetics and the like, and can be produced cheaply and easily.

By the way, the glyceryl-etherified polyhydric alcohols or the hydroxyalkyl-etherified polyhydric alcohols have heretofore been produced by reacting an epoxy compound such as glycidyl ether with a polyhydric alcohol in the presence of a catalyst. Therefore, an etherified polyhydric alcohol is obtained as a mixture of various etherified polyhydric alcohols different from each other in degree of etherification, such as a 1-mol adduct of the polyhydric alcohol obtained by a reaction with 1 mole of the epoxy compound and a 2-mol adduct of the polyhydric alcohol obtained by a reaction with 2 moles of the epoxy compound. However, since the properties of such compounds vary according to a difference in degree of etherification (the mol number added), it is desirable to use etherified polyhydric alcohols each having a uniform degree of etherificaion according to their purposes. For example, the 1-mol adduct is preferred as a cosmetic ingredient. In order to obtain a mixture of containing the 1-mol adduct at a high content level, it is necessary to raise the excess rate of the polyhydric alcohol to the epoxy compound. This is however problematic because the mixture cannot help resulting in lower productivity.

In view of the foregoing circumstances, the present inventors have carried out an extensive investigation. As a result, it has been found that a fatty acid ester (1) of an etherified polyhydric alcohol, which is obtained by reacting a fatty acid ester of a polyhydric alcohol with an epoxy compound and will be described subsequently, is not only useful as an intermediate for the production of an etherified polyhydric alcohol heretofore in use as a cosmetic ingredient in that an etherified polyhydric alcohol having a desired degree of etherification can be efficiently produced via the compound (1), but also excellent per se in the performance as a base, emulsifier, lubricant, oily component and the like for cosmetics, thus leading to completion of the present invention.

DISCLOSURE OF THE INVENTION

According to the present invention, there is thus provided a fatty acid ester of an etherified polyhydric alcohol represented by the following general formula (1):

wherein G represents a residue formed by removing the hydrogen atoms of all the hydroxyl groups of a polyhydric alcohol having at least three hydroxyl groups;

x groups A may be the same or different from one another and individually represent the following formula (2) or (3):

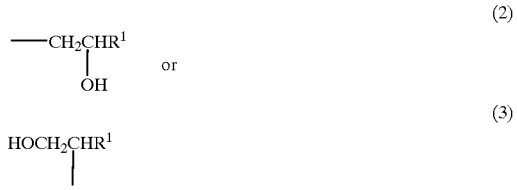

in which $R^1$ represents $R^{1a}$ or $—CH_2OR^{1a}$ ($R^{1a}$: a linear or branched alkyl or alkenyl group having 1–36 carbon atoms);

y groups B may be the same or different from one another and individually represent a hydrogen atom or an acyl group having 1–11 carbon atoms, with the proviso that at least one of y groups B is the acyl group; and x and y individually represent a number of 1 or greater, with the proviso that the sum of x and y amounts to the number of the hydroxyl groups of the polyhydric alcohol corresponding to G.

According to the present invention, there is also provided a process for producing the fatty acid ester (1) of the etherified polyhydric alcohol.

According to the present invention, there is further provided a process for producing an etherified polyhydric alcohol via the fatty acid ester (1) of the etherified polyhydric alcohol.

According to the present invention, there is still further provided a cosmetic composition comprising the fatty acid ester (1) of the etherified polyhydric alcohol.

BEST MODE FOR CARRYING OUT THE INVENTION

The fatty acid ester of the etherified polyhydric alcohol according to the present invention is represented by the general formula (1). Examples of a polyhydric alcohol having at least three hydroxyl groups and corresponding to G in the general formula (1) include pentaerythritol, sorbitol, mannitol, maltitol, glycosides, glycerol, polyglycerols represented by the following formula (4):

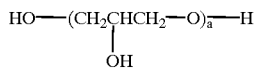
(4)

wherein a represents a number of 2–20, erythritol, inositol, xylitol, dipentaerythritol, tripentaerythritol, heptitol, octitol, 1,2,3,4-pentanetetrol, 1,3,4,5-hexanetetrol, sorbitan, mannitan, raffinose, gentianose, xylose, galactose, mannose, maltose, sorbiose, maltotriose, maltotetraose, maltopentaose, α-cyclodextrin, β-cyclodextrin, γ-cyclodextrin, sucrose, fructofuranose, fructopyranose, glucopyranose and alkylene oxide adducts of these compounds.

Of these, as examples of the glycosides, may be mentioned those obtained by a known means in which (a) a monosaccharide such as glucose, galactose, fructose, mannose or xylose, a disaccharide such as maltose, isomaltose, lactose or sucrose, or a polysaccharide such as cellulose, starch or amylose is reacted with (b) an alcohol such as methanol, ethanol, propanol, octanol, decyl alcohol, dodecyl alcohol, oleyl alcohol or 2-ethylhexanol, or a polyhydric alcohol such as ethylene glycol, propylene glycol, glycerol, erythritol or sorbitol in the presence of a catalyst. As specific examples of the glycosides, may be mentioned alkyl glycosides such as methyl glucoside, ethyl glucoside, propyl glucoside, octyl glucoside, decyl glucoside, dodecyl glucoside, oleyl glucoside, 2-ethylhexyl glucoside, methyl maltoside and ethyl maltoside; hydroxyalkyl glycosides such as 2-hydroxypropyl glucoside, 2,3-dihydroxypropyl glucoside and 2-hydroxyethylglucoside; alkyl ether glycosids such as methoxyethyl glucoside and ethoxyethyl glucoside; and oligosaccharides whose reducible terminals have been reduced, such as maltitol and lactitol.

The polyglycerols (4) are polyglycerols obtained by condensing glycerol by a known method as typified by diglycerol, triglycerol, tetraglycerol, pentaglycerol and the like. The polyglycerols (4) may be polyglycerols having an average condensation degree a of 2–20. However, polyglycerols high in condensation degree may become too high in hydrophilicity to exhibit satisfactory performance in some cases. Therefore, polyglycerols whose a is preferably 2–10, more preferably 2–4 are desirable.

In the alkylene oxide adducts of these polyhydric alcohols, the number of carbon atoms of the alkylene oxide is preferably 2–4, and the average number of moles of the alkylene oxide added is preferably 1–10 moles per hydroxyl group.

Preferable examples of these polyhydric alcohols include pentaerythritol, sorbitol, mannitol, glycosides, glycerol, polyglycerols (4) and the alkylene oxide adducts of these alcohols. Pentaerythritol, glycerol and polyglycerols (4) whose a is 2–4 are more preferred, with pentaerythritol being particularly preferred.

In the general formula (1), A denotes a group represented by the formula (2) or (3). As the alkyl group represented by $R^{1a}$, those having 6–36 carbon atoms are preferred. Of these, branched alkyl groups are more preferred. Particularly preferred alkyl groups include those represented by the following formula (6) or (7):

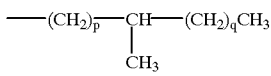
(6)

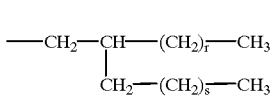
(7)

wherein p and q individually represent an integer of 0–33, with the proviso that the sum of p and q amounts to 13–33, and r and s individually represent an integer of 0–31, with the proviso that the sum of r and s amounts to 11–31. Of these, those represented by the formula (6) are preferred. As the alkenyl group represented by $R^{1a}$, those having 6–36 carbon atoms are preferred, with hexadecenyl and octadecenyl (oleyl) groups, and the like being particularly preferred.

Specific preferable examples of $R^{1a}$ include hexyl, octyl, hexadecyl, methylpentadecyl, methylhexadecyl, methylheptadecyl (isostearyl), methyloctadecyl, methylbehenyl, ethylhexadecyl, ethyloctadecyl, ethylbehenyl, butyldodecyl, butylhexadecyl, butyloctadecyl, hexyldecyl, heptylundecyl, octyldodecyl, decyldodecyl, decyltetradecyl, dodecylhexadecyl, tetradecyloctadecyl, hexadecenyl and octadecenyl (oleyl) groups.

In the general formula (1), y groups B individually represent a hydrogen atom or an acyl group having 1–11 carbon atoms, with the proviso that at least one of y groups B is the acyl group. As the acyl group, linear or branched alkanoyl groups having 2–11 carbon atoms are preferred, with alkanoyl group having 2–4 carbon atoms being particularly preferred.

x and y in the general formula (1) individually represent a number of 1 or greater, with the proviso that the sum of x and y amounts to the number of the hydroxyl groups of the polyhydric alcohol (G).

In the present invention, the production process of the fatty acid ester (1) of the etherified polyhydric alcohol and the production process of the etherified polyhydric alcohol (10) via the fatty acid ester (1) are represented by the following reaction scheme:

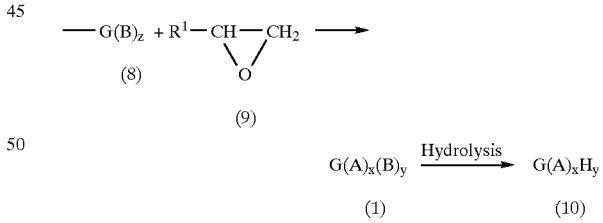

wherein G, A, B, x, y and $R^1$ have the same meaning as defined above, and z represents the number of the hydroxyl groups of the polyhydric alcohol corresponding to G, with the proviso that z groups B contain at least one hydrogen atom and acyl group as a whole.

More specifically, a fatty acid ester (8) of a polyhydric alcohol is reacted with an epoxy compound (9), thereby obtaining a fatty acid ester (1) of an etherified polyhydric alcohol. This fatty acid ester is then hydrolyzed, thereby obtaining an etherified polyhydric alcohol (10).

The fatty acid ester (8) of the polyhydric alcohol useful in the practice of the present invention is synthesized in accordance with any conventionally-known method. For example, a polyhydric alcohol having at least three hydroxyl groups is reacted with a fatty acid, fatty acid ester, fatty acid chloride, fatty acid anhydride or the like at 100–200° C. without any catalyst or in the presence of a catalyst such as p-toluenesulfonic acid, sulfuric acid, sodium hydroxide, potassium hydroxide, sodium acetate or sodium phosphate, preferably sodium acetate without any solvent or in a solvent such as toluene or xylene, thereby obtaining the fatty acid ester (8) of the polyhydric alcohol. The fatty acid ester (8) of the polyhydric alcohol is also obtained by the transesterification of a fatty acid ester of a polyhydric alcohol with a polyhydric alcohol.

The polyhydric alcohols used herein may contain impurities other than the polyhydric alcohol required for obtaining the intended product and may be used as it is so far as it causes no practical problem. If the intended product needs to be improved on need for better functionality, quality and the like, the alcohol may be used in a purified form made by the conventionally-known purification method.

In the case of, for example, pentaerythritol, dipentaerythritol and tripentaerythritol formed by the condensation of pentaerythritol may be contained therein in some cases. Besides, sorbitol and mannitol may contain a small amount of reducing sugars such as glucose in some cases. If such an alcohol is used as it is, a small amount of fatty acid esters of these impurities are formed as by-products. However, the alcohol may be purified by a crystallization process and/or the like, as needed, before use.

As the fatty acid, fatty acid ester, fatty acid chloride, fatty acid anhydride or the like with which these polyhydric alcohols are reacted, any compound of these may be used so far as its fatty acid moiety has 1–11 carbon atoms. However, that having 2–4 carbon atoms, particularly, acetic acid is preferred from the viewpoint of easy after-treatment after the hydrolysis. In the case of the transesterification, an ester obtained by the reaction of the polyhydric alcohol with the fatty acid or the like as described above may be used as the fatty acid ester of the polyhydric alcohol.

The thus-obtained fatty acid ester (8) of the polyhydric alcohol is provided as a mixture of the polyhydric alcohol and various esters such as a monoester with 1 mole of the fatty acid added to the polyhydric alcohol and a diester with 2 moles of the fatty acid added to the polyhydric alcohol. Such a mixture normally involves no reaction-disturbing problem, and may be thereafter used as it is. However, if a specifically high-purified product is desired, the mixture may be subjected to purification by chromatography and/or the like so as to isolate the fatty acid ester (8).

In the case where pentaerythritol monoacetate is produced, the reaction thereof is illustrated as follows. Namely, pentaerythritol is reacted with acetic acid in an amount of 1–3 moles per mole of pentaerythritol at a reflux temperature in the presence of an optional catalyst such as sodium acetate without any solvent or in a solvent such as toluene or xylene in accordance with the following reaction scheme A. Alternatively, pentaerythritol is reacted with pentaerythritol tetraacetate in an amount of 0.1–2 moles per mole of pentaerythritol at a reflux temperature in the presence of an optional catalyst such as sodium acetate without any solvent or in a solvent such as toluene or xylene in accordance with the following reaction scheme B. In each reaction, a mixture composed mainly of pentaerythritol monoacetate can be obtained.

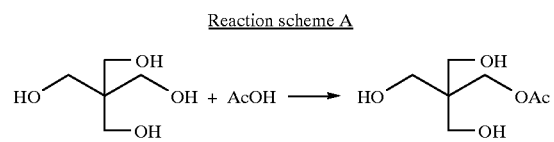

Reaction scheme A

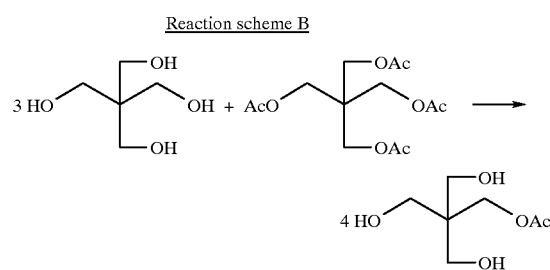

Reaction scheme B

The epoxy compound (9) useful in the practice of the present invention is represented by the following general formula (9a) or (9b):

wherein $R^{1a}$ has the same meaning as defined above. The glycidyl ether represented by the general formula (9b) is preferred.

A molar ratio of the fatty acid ester (8) of the polyhydric alcohol to the epoxy compound (9) in the reaction can be suitably selected according to the intended etherification degree of the fatty acid ester (1) of the etherified polyhydric alcohol. For example, in order to obtain a mixture containing the 1-mol adduct in a high proportion, it is preferable to make the amount of the fatty acid ester (8) of the polyhydric alcohol excess in a ratio of 1.0:1.0–5.0:1.0. In view of the amount of the 1-mol adduct formed and the recovery of the fatty acid ester (9) of the polyhydric alcohol, it is preferable to make the amount of the fatty acid ester (8) of the polyhydric alcohol excess in a ratio of 1.2:1.0–3.0:1.0. In the case where a mixture containing the 2-mol adduct in a high proportion will be obtained, it is preferable to make the amount of the epoxy compound (9) excess in a ratio of 0.4:1.0–1.0:1.0. In view of the amount of the 2-mol adduct formed, it is particularly preferable to make the amount of the epoxy compound (9) excess in a ratio of 0.5:1.0–0.7:1.0.

This reaction may be conducted without any solvent. However, an organic solvent may be used for the purpose of facilitating the mixing of the raw materials. Examples of such a solvent include hexane, toluene, xylene, chloroform, 2-methyl-2-propanol, cyclohexane, ethyl acetate, dimethyl sulfoxide, dimethylacetamide, dimethylformamide and N-methylpyrrolidone. It is preferable to use the solvent 0.1–10.0 times as much as the fatty acid ester (8) of the polyhydric alcohol by weight.

As the catalyst, there may be used an acid catalyst or base catalyst which is generally known as a catalyst for the reaction of an epoxy group. The use of the base catalyst can prevent a decomposition reaction of the ether linkages and a dehydration reaction of the hydroxyl groups of the fatty acid ester (1) of the etherified polyhydric alcohol formed, which are side reactions. It is hence preferable to use the base catalyst. No particular limitation is imposed on the base catalyst. However, sodium hydroxide, potassium hydroxide, sodium methylate, sodium ethylate, sodium hydride, sodium acetate, sodium carbonate and the like are preferred from the viewpoint of reactivity and economy, with sodium acetate being particularly preferred. These base catalysts are preferably used within a range of 0.01–20.0 wt. %, particularly 0.1–10.0 wt. % based on the fatty acid ester of the polyhydric alcohol.

This reaction is conducted at 50–250° C., preferably 80–200° C. If the reaction temperature is lower than 50° C., the reaction rate is slowed down. On the other hand, any reaction temperature of higher than 250° C. causes the reaction product to be pigmented. It is hence not preferable to conduct the reaction at any temperature outside the above range.

In this reaction, the epoxy group of the epoxy compound (9) would be reacted with water if this reaction system contained any water content, and lead to occurrence of undesired by-product such as glyceryl ether. Therefore, it is preferable that the epoxy compound (9) be added and reacted after removing water from the fatty acid ester (8) of the polyhydric alcohol by heating and melting the fatty acid ester (8), or dissolving or dispersing it in an organic solvent, and then introducing dry nitrogen gas into the melt or solution under heat, or dehydrating it by heating under reduced pressure.

Since there are two reaction sites to the epoxy compound (9) in this reaction, the resulting fatty acid ester (1) of the etherified polyhydric alcohol will be a mixture of compounds separately having the groups A of the aforementioned two structures. Namely, in the case where pentaerythritol monoacetate is used as a raw material to obtain the 1-mol adduct, the reaction thereof is illustrated as follows.

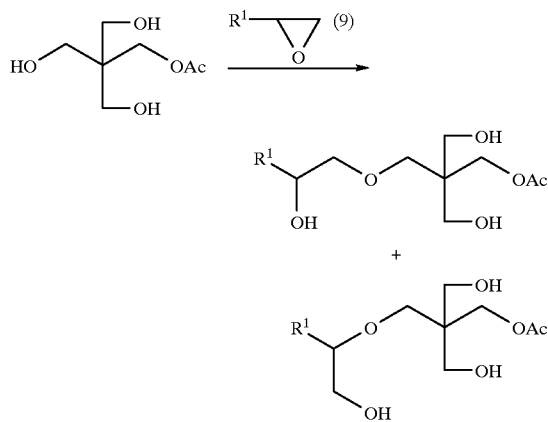

After completion of the reaction, the fatty acid ester (1) of the etherified polyhydric alcohol according to the present invention is obtained from the liquid reaction mixture through methods such as neutralization, filtration, distillation and extraction. However, this product is a mixture composed of various ethers such as a monoetherified product and a dietherified product. The compound (1) according to the present invention may be either incorporated into a cosmetic composition or used as an intermediate for the production of an etherified polyhydric alcohol as the mixture in a non-purified form. However, it may be purified into a monoester or diester suitable for use as a cosmetic ingredient in accordance with a method known per se in the art, such as column chromatography on silica gel and/or solvent extraction before use.

The hydrolysis of the fatty acid ester (1) of the etherified polyhydric alcohol is normally performed in the absence of solvent. However, a solvent may be used so as to enable the reaction to more speedily proceed. No particular limitation is imposed on th e solvent. Preferable examples thereof include methanol, ethanol, 1-propanol, 2-propanol, n-butanol, 2-butanol, 2-methyl-2-propanol, isobutanol, heptanol, hexanol, cyclohexanol, hexane, cyclohexane, methyl ethyl ketone and diisopropyl ketone. The amount of the solvent to be used is preferably within a range of 0.1–10 times, particularly 0.5–3 times to the total weight of the epoxy compound (9).

The hydrolysis is conducted using an acid or base catalyst. The use of the base catalyst can prevent the reesterification of an etherified polyhydric alcohol (10) by a fatty acid s eparated. It is hence preferable to use the base catalyst. No particular limitation is imposed on the base catalyst to be used. However, sodium hydroxide, potassium hydroxide and the like are preferred from the viewpoint of reactivity and economy. It is only necessary to use the base in an amount equal to or more than the ester residue. It is also preferable to use the base in a proportion of 1.0–2.0 moles per mole of the ester residue. These bases may be used in the form of an aqueous solution.

The hydrolysis reaction is preferably conducted at a temperature of 0–100° C., particularly 20–80° C.

After completion of the hydrolysis reaction, the etherified polyhydric alcohol (10) is obtained through the process of removing an excess amount of the base by neutralizing the base with, for example, an organic acid such as acetic acid, citric acid or lactic acid, or an inorganic acid such as sulfuric acid, hydrochloric acid or phosphoric acid, or washing the reaction product with water, and then removing the organic solvent used in the reaction, provided that the reaction is conducted using base catalyst. In order to avoid the thermal decomposition of the reaction product, the organic solvent is preferably removed at a temperature not higher than 130° C. under reduced pressure.

The etherified polyhydric alcohol (10) thus obtained is a mixture of a monoetherified product, a dietherified product and the like. The mixture may be used as a cosmetic ingredient in a non-purified form so far as it causes no practical problem. However, it may be purified for use by any known purification methods such as column chromatography on silica gel and solvent extraction in order to enhance its performance.

When the compound (1) according to the present invention is used as an ingredient for a cosmetic composition, the amount of the compound (1) of the present invention to be incorporated is preferably 0.1–20 wt. %, particularly 0.5–10 wt. % of the cosmetic composition.

In the cosmetic composition according to the present invention, other ingredients commonly used in the classical cosmetic compositions, for example, polyhydric alcohols, such as ethylene glycol, diethylene glycol, triethylene glycol, still higher polyethylene glycols, propylene glycol, dipropylene glycol, still higher polypropylene glycols, butylene glycols such as 1,3-butylene glycol and 1,4-butylene glycol, glycerol, diglycerol, still higher polyglycerols, sugar alcohols such as sorbitol, mannitol, xylitol and maltitol, adducts of glycerols with ethylene oxide (hereinafter abbreviated as "EO"), adducts of glycerols with propylene oxide (hereinafter abbreviated as "PO"), adducts of sugar alcohols with EO or PO, monosaccharides such as galactose, glucose and fructose and adducts of these monosaccharides with EO or PO, and polysaccharides such as maltose and lactose and adducts of these polysaccharides with EO or PO; oily components, such as hydrocarbons such as liquid paraffin, squalane, vaseline and solid paraffin, natural oils such as olive oil, jojoba oil, evening primrose oil, coconut oil and beef tallow, ester oils such as isopropyl myristate, cetyl isooctanoate and glycol neopentyl dicaprate, silicone oils such as methyl silicone and methylphenyl silicone, and higher fatty acids such as isostearic acid and oleic acid; nonionic surfactants such as polyoxyethylene (hereinafter abbreviated as "POE") alkyl ethers, POE branched alkyl ethers, POE sorbitan esters, fatty acid esters of POE glycerol, POE hardened castor oil, sorbitan esters, fatty acid esters of glycerol and fatty acid esters of polyglycerol, anionic surfactants of the phosphoric acid type, sulfonic acid type, sulfuric acid type, carboxylic acid type and the like, and other amphoteric surfactants and cationic surfactants; medicinally-effective ingredients, such as vitamins, disinfectants such as triclosan and triclocarban, antiinflammatory agents such as dipotassium glycyrrhetinate and tocopheryl acetate, antidandruff agents such as zinc pyrithione and octopirox, activators, and ultraviolet absorbents; antiseptics such as methylparaben and butylparaben; foam-increasing agents such as alkylamine oxides and fatty acid alkanolamides, viscosity modifiers such as inorganic salts, polyethylene glycol stearate and ethanol, pearl-like-hue-imparting agents, perfume bases, colorants, and antioxidants; water-swelling clay minerals such as montmorillonite, saponite, hectorite, beagum, cunivia and semitone; other polymers, such as polysaccharides such as karrageenan, xanthan gum, sodium alginate, pullulan, methyl cellulose, carboxymethyl cellulose, hydroxyethyl cellulose and hydroxypropyl cellulose, and synthetic polymers such as carboxyvinyl polymers and polyvinyl pyrrolidone; pigments, such as extender pigments such as titanium oxide, kaolin, mica, sericite, zinc white and talc, and polymeric powders such as poly(methyl methacrylate) powder and nylon powder; and the like, may be suitably incorporated in addition to the compound (1) according to the present invention so far as no detrimental influence is thereby imposed on the effects of the present invention.

The cosmetic composition according to the present invention can be prepared in accordance with a method known per se in the art and may be formulated in any form such as liquid, cream, solid or powder. Particularly, it is preferable that the composition be formulated in the form of liquid or cream.

EXAMPLES

The present invention will hereinafter be described in more detail by the following Examples. However, the present invention is not limited to these examples. In accordance with the present invention, the gas chromatography operations of Referential Examples and Examples below were carried out using a GC-14A (product of Shimadzu Corporation) charged with Silicon SE 1% (2.6 mm in diameter×0.5 m).

Referential Example 1

Synthesis of Pentaerythritol Monoacetate

A 2-liter 4-necked flask was charged with 408 g (3 mol) of pentaerythritol, 309 g (1 mol) of pentaerythritol tetraacetate and 0.4 g of sodium acetate. While stirring in a nitrogen atmosphere, the reactants were reacted at 170° C. for 2 hours, thereby obtaining 717 g of a mixture containing pentaerythritol monoacetate. The composition feature of this mixture was analyzed by gas chromatography. The results thereof are shown in Table 1.

Referential Example 2

Synthesis of Pentaerythritol Monoacetate

A 2-liter 4-necked flask was charged with 544 g (4 mol) of pentaerythritol and 360 g (6 mol) of acetic acid, and the contents were refluxed for 3 hours. Thereafter, acetic acid was distilled off under reduced pressure, thereby obtaining 664 g of a mixture containing pentaerythritol monoacetate. The composition feature of this mixture was analyzed by gas chromatography. The results thereof are shown in Table 1.

TABLE 1

Compositions of mixtures containing pentaerythritol monoacetate (GC AREA %)

| | Referential Example 1 | Referential Example 2 |
|---|---|---|
| Pentaerythritol | 35 | 35 |
| Pentaerythritol monoacetate | 43 | 43 |
| Pentaerythritol diacetate | 19 | 19 |
| Pentaerythritol triacetate | 3 | 3 |
| Pentaerythritol tetraacetate | 0 | 0 |

From Table 1, it proved that there was no difference in composition features between both products of Referential Example 1 and Referential Example 2.

Referential Example 3

Synthesis of Pentaerythritol Diacetate

A 1-liter 4-necked flask was charged with 136 g (1 mol) of pentaerythritol, 304 g (1 mol) of pentaerythritol tetraacetate and 0.4 g of sodium acetate. While stirring in a nitrogen atmosphere, the reactants were reacted at 170° C. for 2 hours, thereby obtaining 440 g of a mixture containing pentaerythritol diacetate. The composition feature of this mixture was analyzed by gas chromatography. The results thereof are shown in Table 2.

TABLE 2

Compositions of a mixture containing pentaerythritol diacetate (GC AREA %)

| | Referential Example 3 |
|---|---|
| Pentaerythritol | 7 |
| Pentaerythritol monoacetate | 29 |
| Pentaerythritol diacetate | 40 |
| Pentaerythritol triacetate | 21 |
| Pentaerythritol tetraacetate | 3 |

Referential Example 4

Synthesis of Pentaerythritol Monobutyrate

A 500-ml 4-necked flask was charged with 136 g of pentaerythritol, 132 g of butyric acid and 0.4 g of sodium acetate, and the contents were refluxed for 2 hours. Thereafter, the solvent was distilled off, thereby obtaining 224 g of a mixture containing pentaerythritol monobutyrate. The composition feature of this mixture was analyzed by gas chromatography. The results thereof are shown in Table 3.

TABLE 3

Compositions of a mixture containing
pentaerythritol monobutyrate (GC AREA %)

|  | Referential Example 4 |
| --- | --- |
| Pentaerythritol | 33 |
| Pentaerythritol monoacetate | 44 |
| Pentaerythritol diacetate | 20 |
| Pentaerythritol triacetate | 3 |
| Pentaerythritol tetraacetate | 0 |

Example 1

A 300-ml 4-necked flask was charged with 71.3 g of the mixture containing pentaerythritol monoacetate obtained in Referential Example 1 and 0.04 g of sodium acetate, and the contents were heated to and melted at 170° C. Thereafter, dry nitrogen gas was introduced into the melt, and 65.2 g of isostearyl glycidyl ether were added dropwise over 30 minutes. The reactants were then reacted at 170° C. for 6 hours with stirring.

The resultant reaction product was then separated and purified by column chromatography on silica gel (eluting solvent: hexane:acetone=1:1), thereby obtaining 34 g (yield: 33%) of pentaerythritol monoisostearyl glyceryl ether monoacetate (purity: at least 99% as determined by liquid chromatography).

Saponification value: 112 (calculated value: 111)

$^1$H-NMR (CDCl$_3$): δ (ppm); 3.3–4.0(m,—OCH$_2$—, —CHOH—), 2.1(s,—OCOCH$_3$), 1.3–1.6(b,—CH$_2$—, —CH—), 0.9(m,—CH$_3$). IR (liquid film) cm$^{-1}$: ν(—OH) 3200–3400; ν(stretching) (—CH—,—CH$_2$—,—CH$_3$) 2850, 2920; ν(C=O) 1750, 1250; ν(deformation) (—CH—, —CH$_2$—, —CH$_3$) 1375, 1460; ν(—C—O—) 1110, 1035, 1010.

Example 2

A 200-ml 4-necked flask was charged with 44 g of the mixture containing pentaerythritol diacetate obtained in Referential Example 3 and 0.21 g of sodium acetate, and the contents were heated to and melted at 130° C. Thereafter, dry nitrogen gas was introduced into the melt, and 33 g of isostearyl glycidyl ether were added dropwise over 30 minutes. The reactants were then reacted at 170° C. for 6 hours with stirring.

The resultant reaction product was then separated and purified by column chromatography on silica gel (eluting solvent: hexane:acetone=1:1), thereby obtaining 20 g (yield: 37%) of pentaerythritol monoisostearyl glyceryl ether diacetate (purity: at least 99% as determined by liquid chromatography).

Saponification value: 205 (calculated value: 206)

$^1$H-NMR (CDCl$_3$): δ (ppm); 3.3–4.1(m,—OCH$_2$—, —CHOH—), 2.1(s,—OCOCH$_3$), 2.2(s,—OCOCH$_3$), 1.3–1.6(b,—CH$_2$—,—CH—), 0.9(m,—CH$_3$). IR (liquid film) cm$^{-1}$: ν(—OH) 3200–3400; ν(stretching) (—CH—, —CH$_2$—, —CH$_3$) 2850, 2920; ν(C=O) 1740, 1250; ν(deformation) (—CH—,—CH$_2$—,—CH$_3$) 1375, 1460; ν(—C—O—) 1110, 1035, 1010.

Example 3

A 200-ml 4-necked flask was charged with 35.7 g of the mixture containing pentaerythritol monoacetate obtained in Referential Example 2 and 0.02 g of sodium acetate, and the contents were heated to and melted at 170° C. Thereafter, dry nitrogen gas was introduced into the melt, and 18.6 g of octyl glycidyl ether were added dropwise over 30 minutes. The reactants were then reacted at 170° C. for 6 hours with stirring.

The resultant reaction product was then separated and purified by column chromatography on silica gel (eluting solvent: hexane:acetone=1:1), thereby obtaining 12 g (yield: 34%) of pentaerythritol monooctyl glyceryl ether monoacetate (purity: at least 99% as determined by liquid chromatography).

Saponification value: 155 (calculated value: 114)

$^1$H-NMR (CDCl$_3$): δ (ppm); 3.3–4.0(m,—OCH$_2$—, —CHOH—), 2.1(s,—OCOCH$_3$), 1.3–1.6(b,—CH$_2$—, —CH—), 0.9(m,—CH$_3$). IR (liquid film) cm$^{-1}$: ν(—OH) 3200–3400; ν(stretching) (—CH—,—CH$_2$—,—CH$_3$) 2850, 2920; ν(C=O) 1750, 1250; ν(deformation) (—CH—, —CH$_2$—, —CH$_3$) 1375, 1460; ν(—C—O—) 1110, 1035, 1010.

Example 4

A 200-ml 4-necked flask was charged with 41 g of the mixture containing pentaerythritol monobutyrate obtained in Referential Example 4 and 0.02 g of sodium acetate, and the contents were heated to and melted at 130° C. Thereafter, dry nitrogen gas was introduced into the melt, and 33 g of stearyl glycidyl ether were added dropwise over 30 minutes. The reactants were then reacted at 130° C. for 6 hours with stirring.

The resultant reaction product was then separated and purified by column chromatography on silica gel (eluting solvent: hexane:acetone=1:1), thereby obtaining 18 g (yield: 34%) of pentaerythritol monostearyl glyceryl ether monobutyrate (purity: at least 99% as determined by liquid chromatography).

Saponification value: 105 (calculated value: 105)

$^1$H-NMR (CDCl$_3$): δ (ppm); 3.3–4.0(m,—OCH$_2$—, —CHOH—), 2.2(q,—OCOCH$_3$), 1.3–1.6(b,—CH$_2$—, —CH—), 1.0(m,—CH$_3$). IR (liquid film) cm$^{-1}$: ν(—OH) 3200–3400; ν(stretching) (—CH—,—CH$_2$—,—CH$_3$) 2850, 2920; ν(C=O) 1740, 1250; ν(deformation) (—CH—, —CH$_2$—, —CH$_3$) 1375, 1460; ν(—C—O—) 1110, 1035, 1010.

Example 5

A 300-ml 4-necked flask was charged with 70.9 g of the mixture containing pentaerythritol monoacetate obtained in Referential Example 1 and 0.04 g of sodium acetate, and the contents were heated to and melted at 170° C. Thereafter, dry nitrogen gas was introduced into the melt, and 64.3 g of oleyl glycidyl ether were added dropwise over 30 minutes. The reactants were then reacted at 170° C. for 6 hours with stirring.

The resultant reaction product was then separated and purified by column chromatography on silica gel (eluting solvent: hexane:acetone=1:1), thereby obtaining 30 g (yield: 30%) of pentaerythritol monooleyl glyceryl ether monoacetate (purity: at least 99% as determined by liquid chromatography).

Saponification value: 112 (calculated value: 111)

$^1$H-NMR (CDCl$_3$): δ (ppm); 5.34(m,—CH=CH—), 4.05 (s,—CH$_2$—OCO—), 3.3–4.0(m,—OCH$_2$—,—CHOH—), 2.03(b,—CH$_2$—C=), 1.8(s,—OCOCH$_3$), 1.3–1.6(b, —CH$_2$—, —CH—), 0.9(m,—CH$_3$). IR (liquid film) cm$^{-1}$: ν(—OH) 3200–3400; ν(alkene CH stretching) 3048; ν(stretching) (—CH—,—CH$_2$—,—CH$_3$) 2850, 2920;

$\nu(C=O)$ 1750, 1250; $\nu(C=C$ stretching) 1644; $\nu$(deformation) (—CH—,—CH$_2$—,—CH$_3$) 1375, 1460; $\nu$(—C—O—) 1110, 1035, 1010.

Example 6

A 200-ml 4-necked flask was charged with 48 g of the mixture containing pentaerythritol monoacetate obtained in Referential Example 1 and 0.1 g of sodium acetate, and the contents were heated to and melted at 170° C. Thereafter, dry nitrogen gas was introduced into the melt, and 27 g of 2-hexadecyloxirane were added dropwise over 30 minutes. The reactants were then reacted at 170° C. for 6 hours with stirring.

The resultant reaction product was then separated and purified by column chromatography on silica gel (eluting solvent: hexane:acetone=1:2), thereby obtaining 13 g (yield: 30%) of mono-2-hydroxystearyl pentaerythryl ether monoacetate (purity: at least 99% as determined by liquid chromatography).

Saponification value: 139 (calculated value: 139)

$^1$H-NMR (CDCl$_3$): δ (ppm); 3.3–4.0(m,—OCH$_2$—, —CHOH—), 2.1(s,—OCOCH$_3$), 1.3–1.7(b,—CH$_2$—), 0.9 (m,—CH$_3$). IR (liquid film) cm$^{-1}$: $\nu$(—OH) 3200–3400; $\nu$(stretching) (—CH—,—CH$_2$—,—CH$_3$) 2860, 2920; $\nu$(C=O) 1750, 1250; $\nu$(deformation) (—CH—,—CH$_2$—, —CH$_3$) 1380, 1460; $\nu$(—C—O—) 1110, 1040, 1005.

Example 7

The compounds according to the present invention obtained in Examples 1–6 were separately used to prepare hair rinse compositions having their corresponding composition features shown in Table 4. The performance of these rinse compositions were investigated. The results are shown in Table 4.

(Preparation process)

After ingredients heated to and melted at 70° C. were added to water heated to the same temperature and stirred into a mixture, the mixture was cooled down to room temperature with stirring, thereby obtaining a hair rinse composition.

(Evaluation method)

Each about 20 g (15 cm long) of the hair of Japanese women, which had not been subjected to any hairdressing treatment such as cold permanent waving or bleaching, was bound up. This hair bundle was subjected to a washing treatment with a commercially-available shampoo comprising, as a main component, an anionic surfactant. Two grams of each of the hair rinse compositions shown in Table 4 were applied evenly to the hair bundle thus shampooed and then rinsed out for 30 seconds with running water. The thus-treated hair bundle was then towelled dry. With respect to the hair bundle of this wet state, the softness, smoothness and oily feeling were organoleptically evaluated and ranked in accordance with the following evaluation standard:

⊚: Excellent;

○: Good;

Δ: Acceptable; and x: Poor.

TABLE 4

| Ingredient (wt. %) | Invention product | | | | | | Comparative product | | | | |
|---|---|---|---|---|---|---|---|---|---|---|---|
| | 1 | 2 | 3 | 4 | 5 | 6 | 1 | 2 | 3 | 4 | 5 |
| Pentaerythritol isostearyl glyceryl ether monoacetate (Example 1) | 3.0 | | | | | | | | | | |
| Pentaerythritol isostearyl glyceryl ether diacetate (Example 2) | | 3.0 | | | | | | | | | |
| Pentaerythritol octyl glyceryl ether monoacetate (Example 3) | | | 3.0 | | | | | | | | |
| Pentaerythritol isostearyl glyceryl ether monobutyrate (Example 4) | | | | 3.0 | | | | | | | |
| Pentaerythritol oleyl glyceryl ether monoacetate (Example 5) | | | | | 3.0 | | | | | | |
| 2-Hydroxystearyl pentaerythyl ether monoacetate (Example 6) | | | | | | 3.0 | | | | | |
| Stearyl glyceryl ether (Comparative product) | | | | | | | 3.0 | | | | |
| Isostearyl alocohol (Comarative product) | | | | | | | | 3.0 | | | |
| Polyoxyethylene (20 mol) oleyl ether (Comparative product) | | | | | | | | | 3.0 | | |
| Polyoxyethylene (9 mol) stearate (Comparative product) | | | | | | | | | | 3.0 | |
| Polyoxyethylene (20 mol) sorbitan monolaurate (Comparative product) | | | | | | | | | | | 3.0 |
| Stearyltrimethylammonium chloride | 2.0 | 2.0 | 2.0 | 2.0 | 2.0 | 2.0 | 2.0 | 2.0 | 2.0 | 2.0 | 2.0 |
| Ion-exchanged water | 95.0 | 95.0 | 95.0 | 95.0 | 95.0 | 95.0 | 95.0 | 95.0 | 95.0 | 95.0 | 95.0 |
| Evaluation  Softness | ⊚ | ⊚ | ⊚ | ⊚ | ⊚ | ⊚ | Δ | Δ | Δ | ○ | ○ |
| Smoothness | ⊚ | ⊚ | ⊚ | ⊚ | ⊚ | ⊚ | ○ | ○ | ○ | ○ | Δ |
| Littleness of an oily feeling | ⊚ | ⊚ | ⊚ | ⊚ | ⊚ | ⊚ | Δ | x | ○ | Δ | ○ |

Preparation Example 1

A 3-liter 4-necked flask was charged with 713 g of the mixture containing pentaerythritol monoacetate obtained in Referential Example 1 and 0.41 g of sodium acetate, and the contents were heated to and melted at 170° C. Thereafter, dry nitrogen gas was introduced into the melt, and 652 g of isostearyl glycidyl ether were added dropwise over 30 minutes. The reactants were then reacted at 170° C. for 6 hours with stirring.

After completion of the reaction, 924 g of n-butanol and 1,100 g of a 16% aqueous solution of sodium hydroxide were added to conduct hydrolysis at 70° C. for 1 hour. After the liquid reaction mixture was separated into layers, an organic layer was washed with 1,600 g of a 0.5% aqueous solution of Glauber's salt, and n-butanol was distilled out of the organic layer, thereby obtaining 840 g of isostearyl glyceryl-etherified pentaerythritol.

The composition feature of this product was analyzed by gas chromatography. The results thereof are shown in Table 5.

Preparation Example 2

A 200-ml 4-necked flask was charged with 44 g of the mixture containing pentaerythritol diacetate obtained in Referential Example 3 and 0.21 g of sodium acetate, and the contents were heated to and melted at 130° C. Thereafter, dry nitrogen gas was introduced into the melt, and 33 g of isostearyl glycidyl ether were added dropwise over 30 minutes. The reactants were then reacted at 130° C. for 6 hours with stirring.

After completion of the reaction, 47 g of n-butanol and 110 g of a 16% aqueous solution of sodium hydroxide were added to conduct hydrolysis at 70° C. for 1 hour. After the liquid reaction mixture was separated into layers, an organic layer was washed with 160 g of a 0.5% aqueous solution of Glauber's salt, and n-butanol was distilled out of the organic layer, thereby obtaining 42 g of isostearyl glyceryl-etherified pentaerythritol.

The composition feature of this product was analyzed by gas chromatography. The results thereof are shown in Table 5.

Preparation Example 3

A 200-ml 4-necked flask was charged with 44 g of the mixture containing pentaerythritol diacetate obtained in Referential Example 3 and 0.21 g of sodium acetate, and the contents were heated to and melted at 170° C. Thereafter, dry nitrogen gas was introduced into the melt, and 33 g of isostearyl glycidyl ether were added dropwise over 30 minutes. The reactants were then reacted at 170° C. for 6 hours with stirring.

After completion of the reaction, 47 g of n-butanol and 110 g of a 16% aqueous solution of sodium hydroxide were added to conduct hydrolysis at 70° C. for 1 hour. After the liquid reaction mixture was separated into layers, an organic layer was washed with 160 g of a 0.5% aqueous solution of Glauber's salt, and n-butanol was distilled out of the organic layer, thereby obtaining 42 g of isostearyl glyceryl-etherified pentaerythritol.

The composition feature of this product was analyzed by gas chromatography. The results thereof are shown in Table 5.

Comparative Preparation Example 1

A 5-liter 4-necked flask was charged with 1,090 g of pentaerythritol, 2,720 g of dimethyl sulfoxide and 16.3 g of a 48% aqueous solution of sodium hydroxide, and the contents were heated to 90° C. into a solution. Thereafter, about 120 g of a mixture of water and dimethyl sulfoxide were distilled off under reduced pressure, thereby removing water in the reaction system. After dry nitrogen was then introduced into the solution, and the solution was heated to 110° C., 652 g of isostearyl glycidyl ether were added dropwise over 2 hours. The reactants were then reacted at 110° C. for 3 hours with stirring.

After completion of the reaction, 9.7 g of sulfuric acid were added to the liquid reaction mixture to neutralize the catalyst. Dimethyl sulfoxide was then completely distilled off at 80° C. under reduced pressure, and 99% ethanol was added to the residue so as to separate unreacted pentaerythritol thus deposited by filtration. After ethanol was distilled under reduced pressure out of the thus-obtained filtrate, 1,000 ml of ethyl acetate and 1,000 ml of water were added to the residue, thereby conducting an extraction process. After separation of layers, ethyl acetate was distilled out of an organic layer, thereby obtaining 842 g of isostearyl glyceryl-etherified pentaerythritol.

The composition feature of this product was analyzed by gas chromatography. The results thereof are shown in Table 5.

Comparative Preparation Example 2

In the same manner as in Comparative Preparation Example 1 except that the amount of pentaerythritol to be used was changed to 545 g, and the reaction was conducted at 170° C., 780 g of isostearyl glyceryl-etherified pentaerythritol were obtained.

The composition feature of this product was analyzed by gas chromatography. The results thereof are shown in Table 5.

TABLE 5

|  | Prepn Ex. 1 | Prepn Ex. 2 | Prepn Ex. 3 | Comparative Prepn Ex. 1 | Comparative Prepn Ex. 2 |
| --- | --- | --- | --- | --- | --- |
| 1-Mol glycidyl ether adduct | 78% | 77% | 77% | 76% | 49% |
| 2-Mol glycidyl ether adduct | 19% | 18% | 18% | 20% | 12% |
| Excess rate* | 2 mol/mol | 2 mol/mol | 2 mol/mol | 4 mol/mol | 2 mol/mol |

*: An excess rate of the fatty acid ester of the polyhydric alcohol or the polyhydric alcohol to the glycidyl ether.

Preparation Example 4

A 200-ml 4-necked flask was charged with 53.6 g of a mixture containing glycerol monoacetate obtained in the same manner as in Referential Example 2 except that 4 moles of glycerol were used in place of pentaerythritol, and 0.4 g of sodium hydroxide, and the contents were heated to 130° C. into a solution. Thereafter, dry nitrogen gas was introduced into the solution, and 37.2 g of octyl glycidyl ether were added dropwise over 2 hours. The reactants were then reacted at 130° C. for 4 hours with stirring.

After completion of the reaction, 100 g of hexane and 110 g of a 16% aqueous solution of sodium hydroxide were added to conduct hydrolysis at 70° C. for 1 hour. After the liquid reaction mixture was separated into layers, an organic layer was washed with 160 g of a 0.5% aqueous solution of Glauber's salt, and hexane was distilled out of the organic layer, thereby obtaining 60.9 g of octyl glyceryl-etherified glycerol.

The composition feature of this product was analyzed by gas chromatography. The results thereof are shown in Table 6.

Comparative Preparation Example 3

A 2-liter 4-necked flask was charged with 920 g of glycerol and 8.0 g of an aqueous solution of sodium hydroxide, and the contents were heated to 110° C. into a solution. Thereafter, about 20 g of a mixture of water and glycerol were distilled off under reduced pressure, thereby removing water in the reaction system. After dry nitrogen was then introduced into the solution, and the solution was heated to 110° C., 37.2 g of octyl glycidyl ether were added dropwise over 2 hours. The reactants were then reacted at 110° C. for 5 hours with stirring.

After completion of the reaction, 9.9 g of sulfuric acid were added to the liquid reaction mixture to neutralize the catalyst. Glycerol was then completely distilled off under reduced pressure, and 300 ml of ethyl acetate and 1,000 ml of water were added to the residue, thereby conducting an extraction process. After separation of layers, ethyl acetate was distilled out of an organic layer, thereby obtaining 60.2 g of octyl glyceryl-etherified glycerol.

The composition feature of this product was analyzed by gas chromatography. The results thereof are shown in Table 6.

TABLE 6

| | Preparation Example 4 | Comparative Preparation Example 3 |
|---|---|---|
| 1-Mol glycidyl ether adduct | 77% | 76% |
| 2-Mol glycidyl ether adduct | 18% | 19% |
| Excess rate* | 2 mol/mol | 5 mol/mol |

*: An excess rate of the fatty acid ester of the polyhydric alcohol or the polyhydric alcohol to the glycidyl ether.

Preparation Example 5

A 500-ml flask was charged with 94.4 g of a mixture containing methyl glucoside monoacetate obtained in the same manner as in Referential Example 2 except that 4 moles of methyl glucoside were used in place of pentaerythritol, 200 g of dimethyl sulfoxide and 2.8 g of potassium hydroxide, and the contents were heated to 120° C. into a solution. Dry nitrogen gas was introduced into the solution, and about 20 g of a mixture of water and dimethyl sulfoxide were distilled off, thereby removing water in the reaction system. After 33 g of 2-heptylundecyl glycidyl ether were added dropwise to the residue over 2 hours in the flask, the reactants were reacted at 120° C. for 6 hours with stirring.

After completion of the reaction, 200 g of isobutanol and 110 g of a 16% aqueous solution of sodium hydroxide were added to conduct hydrolysis at 30° C. for 1 hour. After the liquid reaction mixture was separated into layers, an organic layer was washed with 160 g of a 0.5% aqueous solution of Glauber's salt, and isobutanol was distilled out of the organic layer, thereby obtaining 56 g of 2-heptylundecyl glyceryl-etherified methyl glucoside.

The composition feature of this product was analyzed by gas chromatography. The results thereof are shown in Table 7.

Comparative Preparation Example 4

A 1-liter flask was charged with 194 g of methyl glucoside, 400 g of dimethyl sulfoxide and 2.8 g of potassium hydroxide, and the contents were heated to 120° C. into a solution. Dry nitrogen gas was introduced into the solution, and about 50 g of a mixture of water and dimethyl sulfoxide were distilled off, thereby removing water in the reaction system. After 33 g of 2-heptylundecyl glycidyl ether were added dropwise to the residue over 2 hours in the flask, the reactants were reacted at 120° C. for 6 hours with stirring.

After completion of the reaction, 3 g of acetic acid were added to the reaction mixture to neutralize the catalyst. Dimethyl sulfoxide was then completely distilled off at 80° C. under reduced pressure, and 1,000 ml of ethanol were added to the residue so as to separate methyl glucoside thus deposited by filtration. Ethanol was distilled out of the thus-obtained filtrate, thereby obtaining 56 g of 2-heptylundecyl glyceryl-etherified methyl glucoside.

The composition feature of this product was analyzed by gas chromatography. The results thereof are shown in Table 7.

TABLE 7

| | Preparation Example 5 | Comparative Preparation Example 4 |
|---|---|---|
| 1-Mol glycidyl ether adduct | 85% | 84% |
| 2-Mol glycidyl ether adduct | 12% | 13% |
| Excess rate* | 4 mol/mol | 10 mol/mol |

*: An excess rate of the fatty acid ester of the polyhydric alcohol or the polyhydric alcohol to the glycidyl ether.

Preparation Example 6

A 300-ml flask was charged with 95 g of a mixture containing tetraglycerol monoacetate obtained in the same manner as in Referential Example 2 except that 4 moles of tetraglycerol were used in place of pentaerythritol, and 1.08 g of potassium hydroxide, and the contents were heated to 100° C. into a solution. Thereafter, dry nitrogen gas was introduced into the solution, and 33 g of isostearyl glycidyl ether were added dropwise into the flask over 2 hours. The reactants were then reacted at 110° C. for 4 hours with stirring.

After completion of the reaction, 100 g of n-butanol and 110 g of a 16% aqueous solution of sodium hydroxide were added to conduct hydrolysis at 70° C. for 1 hour. After the liquid reaction mixture was separated into layers, an organic layer was washed with 160 g of a 0.5% aqueous solution of Glauber's salt, and isobutanol was distilled out of the organic layer, thereby obtaining 61 g of isostearyl glyceryl-etherified tetraglycerol.

The composition feature of this product was analyzed by gas chromatography. The results thereof are shown in Table 8.

Comparative Preparation Example 5

A 300-ml flask was charged with 157 g of tetraglycerol, 100 g of N-methylpyrrolidone and 1.0 g of potassium hydroxide, and the contents were heated to 100° C. into a solution. Dry nitrogen gas was introduced into the solution, and about 10 g of a mixture of water and N-methylpyrrolidone were distilled off, thereby removing water in the reaction system. After 33 g of isostearyl glycidyl ether were added dropwise to the residue over 5 hours in the flask, the reactants were reacted at 110° C. for 4 hours with stirring.

After completion of the reaction, 1.5 g of acetic acid were added to the reaction mixture to neutralize the catalyst. N-methylpyrrolidone was then completely distilled off at 80° C. under reduced pressure, and 500 ml of methyl ethyl ketone and 1,000 ml of water were added to the residue, thereby conducting an extraction process. Methyl ethyl ketone was distilled out of the methyl ethyl ketone-soluble part thus obtained, thereby obtaining 61 g of isostearyl glyceryl-etherified tetraglycerol.

The composition feature of this product was analyzed by gas chromatography. The results thereof are shown in Table 8.

TABLE 8

|  | Preparation Example 6 | Comparative Preparation Example 5 |
|---|---|---|
| 1-Mol glycidyl ether adduct | 84% | 82% |
| 2-Mol glycidyl ether adduct | 13% | 14% |
| Excess rate* | 4 mol/mol | 8 mol/mol |

*: An excess rate of the fatty acid ester of the polyhydric alcohol or the polyhydric alcohol to the glycidyl ether.

TABLE 9

|  | Preparation Example 7 | Comparative Preparation Example 6 |
|---|---|---|
| 1-Mol oxirane adduct | 78% | 50% |
| 2-Mol oxirane adduct | 18% | 14% |
| Excess rate* | 2 mol/mol | 2 mol/mol |

*: An excess rate of the fatty acid ester of the polyhydric alcohol or the polyhydric alcohol to the oxirane.

Preparation Example 7

A 3-liter 4-necked flask was charged with 713 g of the mixture containing pentaerythritol monoacetate obtained in Referential Example 2 and 0.41 g of sodium acetate, and the contents were heated to and melted at 170° C. Thereafter, dry nitrogen gas was introduced into the melt, and 256 g of 2-hexyloxirane were added dropwise over 30 minutes. The reactants were then reacted at 170° C. for 6 hours with stirring.

After completion of the reaction, 600 g of n-butanol and 1,100 g of a 16% aqueous solution of sodium hydroxide were added to conduct hydrolysis at 80° C. for 1 hour. After the liquid reaction mixture was separated into layers, an organic layer was washed with 1,600 g of a 0.5% aqueous solution of Glauber's salt, and butanol was distilled out of the organic layer, thereby obtaining 475 g of 2-hydroxyoctyl-etherified pentaerythritol.

The composition feature of this product was analyzed by gas chromatography. The results thereof are shown in Table 9.

Comparative Preparation Example 6

A 5-liter 4-necked flask was charged with 545 g of pentaerythritol, 2,720 g of dimethyl sulfoxide and 16.3 g of a 48% aqueous solution of sodium hydroxide, and the contents were heated to 90° C. into a solution. Thereafter, about 120 g of a mixture of water and dimethyl sulfoxide were distilled off under reduced pressure, thereby removing water in the reaction system. After dry nitrogen was then introduced into the solution, and the solution was heated to 170° C., 256 g of 2-hexyloxirane were added dropwise over 2 hours. The reactants were then reacted at 170° C. for 3 hours with stirring.

After completion of the reaction, 9.7 g of sulfuric acid were added to the liquid reaction mixture to neutralize the catalyst. Dimethyl sulfoxide was then completely distilled off at 80° C. under reduced pressure, and 99% ethanol was added to the residue so as to separate unreacted pentaerythritol thus deposited by filtration. After ethanol was distilled under reduced pressure out of the thus-obtained filtrate, 1,000 ml of ethyl acetate and 1,000 ml of water were added to the residue, thereby conducting an extraction process. After separation of layers, ethyl acetate was distilled out of an organic layer, thereby obtaining 410 g of 2-hydroxyoctyl-etherified pentaerythritol.

The composition feature of this product was analyzed by gas chromatography. The results thereof are shown in Table 9.

Preparation Example 8

A 3-liter 4-necked flask was charged with 704 g of the mixture containing pentaerythritol monoacetate obtained in Referential Example 1 and 0.4 g of sodium acetate, and the contents were heated to and melted at 170° C. Thereafter, dry nitrogen gas was introduced into the melt, and 647 g of oleyl glycidyl ether were added dropwise over 30 minutes. The reactants were then reacted at 170° C. for 6 hours with stirring.

After completion of the reaction, 920 g of n-butanol and 1,100 g of a 16% aqueous solution of sodium hydroxide were added to conduct hydrolysis at 70° C. for 1 hour. After the liquid reaction mixture was separated into layers, an organic layer was washed with 1,600 g of a 0.5% aqueous solution of Glauber's salt, and n-butanol was distilled out of the organic layer, thereby obtaining 810 g of oleyl glyceryl-etherified pentaerythritol.

The composition feature of this product was analyzed by gas chromatography. The results thereof are shown in Table 10.

Comparative Preparation Example 7

A 5-liter 4-necked flask was charged with 1,090 g of pentaerythritol, 2,720 g of dimethyl sulfoxide and 16.3 g of a 48% aqueous solution of sodium hydroxide, and the contents were heated to 90° C. into a solution. Thereafter, about 120 g of a mixture of water and dimethyl sulfoxide were distilled off under reduced pressure, thereby removing water in the reaction system. After dry nitrogen was then introduced into the solution, and the solution was heated to 110° C., 648 g of oleyl glycidyl ether were added dropwise over 2 hours. The reactants were then reacted at 110° C. for 3 hours with stirring.

After completion of the reaction, 9.5 g of sulfuric acid were added to the liquid reaction mixture to neutralize the catalyst. Dimethyl sulfoxide was then completely distilled off at 80° C. under reduced pressure, and 99% ethanol was added to the residue so as to separate unreacted pentaerythritol thus deposited by filtration. After ethanol was distilled under reduced pressure out of the thus-obtained filtrate, 1,000 ml of ethyl acetate and 1,000 ml of water were added to the residue, thereby conducting an extraction process. After separation of layers, ethyl acetate was distilled out of an organic layer, thereby obtaining 833 g of oleyl glyceryl-etherified pentaerythritol.

The composition feature of this product was analyzed by gas chromatography. The results thereof are shown in Table 10.

TABLE 10

|  | Preparation Example 8 | Comparative Preparation Example 7 |
|---|---|---|
| 1-Mol glycidyl ether adduct | 80% | 77% |
| 2-Mol glycidyl ether adduct | 14% | 18% |
| Excess rate* | 2 mol/mol | 4 mol/mol |

*: An excess rate of the fatty acid ester of the polyhydric alcohol or the polyhydric alcohol to the glycidyl ether.

INDUSTRIAL APPLICABILITY

The fatty acid esters (1) of the etherified polyhydric alcohols according to the present invention are not only useful as intermediates for the production of etherified polyhydric alcohols used as cosmetic ingredients in that an etherified polyhydric alcohol having a desired degree of etherification can be efficiently produced via the compound (1), but also excellent per se in the performance as bases, emulsifiers, lubricants, oily components and the like for cosmetics.

We claim:

1. A fatty acid ester of an etherified polyhydric alcohol represented by the following general formula (1):

     (1)

wherein G represents a residue formed by removing the hydrogen atoms of all the hydroxyl groups of a polyhydric alcohol having at least three hydroxyl groups;

x groups A may be the same or different from one another and individually represent the following formula (2) or (3):

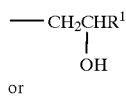     (2)

or

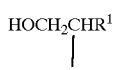     (3)

in which $R^1$ represents $R^{1a}$ or —$CH_2OR^{1a}$, wherein $R^{1a}$ is a linear or branched alkyl group having 1–36 carbon atoms or a linear or branched alkenyl group having 1–36 carbon atoms, y groups B may be the same or different from one another and individually represent a hydrogen atom or a linear or branched alkanoyl group having 2–11 carbon atoms, with the proviso that at least one of y groups B is said linear or branched alkanoyl group having 2–11 carbon atoms; and x and y individually represent a number of 1 or greater, with the proviso that the sum of x and y amounts to the number of the hydroxyl groups of the polyhydric alcohol corresponding to G.

2. The fatty acid ester of an etherified polyhydric alcohol according to claim 1, wherein B in the general formula (1) is a hydrogen atom or a linear or branched alkanoyl group having 2–4 carbon atoms.

3. The fatty acid ester of an etherified polyhydric alcohol according to claim 1, wherein G in the general formula (1) is a residue formed by removing the hydrogen atoms of all the hydroxyl groups of a polyhydric alcohol selected from the group consisting of pentaerythritol, sorbitol, mannitol, a glycoside, glycerol, and a polyglycerol represented by the following formula (4):

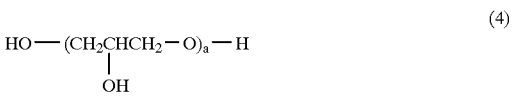     (4)

wherein a represents a number of 2–20, and an alkylene oxide adduct thereof.

4. The fatty acid ester of an etherified polyhydric alcohol according to claim 1, wherein G in the general formula (1) is a residue formed by removing the hydrogen atoms of all the hydroxyl groups of a polyhydric alcohol selected from the group consisting of pentaerythritol, glycerol, and a polyglycerol represented by the following formula (5):

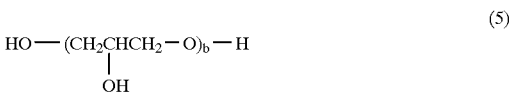     (5)

wherein b represents a number of 2–4.

5. The fatty acid ester of an etherified polyhydric alcohol according to claim 1, wherein $R^{1a}$ is an alkyl group represented by the following formula (6) or (7):

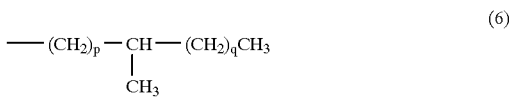     (6)

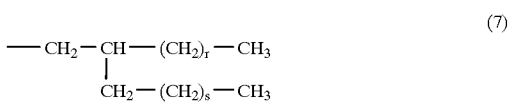     (7)

wherein p and q individually represent an integer of 0–33, with the proviso that the sum of p and q amounts to 13–33, and r and s individually represent an integer of 0–31, with the proviso that the sum of r and s amounts to 11–31.

6. The fatty acid ester of an etherified polyhydric alcohol according to claim 1, wherein $R^{1a}$ is an oleyl group.

7. The fatty acid ester of an etherified polyhydric alcohol according to claim 1, wherein $R^{1a}$ is a linear or branched alkyl group having 6–36 carbon atoms or a linear or branched alkenyl group having 6–36 carbon atoms.

8. A process for producing a fatty acid ester of an etherified polyhydric alcohol represented by the following general formula (1):

     (1)

wherein G represents a residue formed by removing the hydrogen atoms of all the hydroxyl groups of a polyhydric alcohol having at least three hydroxyl groups;

x groups A may be the same or different from one another and individually represent the following formula (2) or (3):

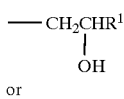

(2)

(3)

in which $R^1$ represents $R^{1a}$ or $-CH_2OR^{1a}$, wherein
$R^{1a}$ is a linear or branched alkyl group having 1–36 carbon atoms or a linear or branched alkenyl group having 1–36 carbon atoms, y groups B may be the same or different from one another and individually represent a hydrogen atom or a linear or branched alkanoyl group having 2–11 carbon atoms, with the proviso that at least one of y groups B is said linear or branched alkanoyl group having 2–11 carbon atoms; and x and y individually represent a number of 1 or greater, with the proviso that the sum of x and y amounts to the number of the hydroxyl groups of the polyhydric alcohol corresponding to G, said process comprising:
reacting a fatty acid ester of a polyhydric alcohol represented by the following general formula (8):

$$G(B)_z \quad (8)$$

wherein G and B have the same meanings as defined above; and z represents the sum of x and y, with the proviso that z groups B contain at least one hydrogen atom and linear or branched alkanoyl group having 2–11 carbon atoms as a whole, with an epoxy compound represented by the following general formula (9):

(9)

$R^1-CH-CH_2$
 \  /
  O wherein $R^1$ has the same meaning as defined above.

9. The process of claim 8, wherein B in the general formula (1) is a hydrogen atom or a linear or branched alkanoyl group having 2–4 carbon atoms.

10. The process of claim 8, wherein G in the general formula (1) is a residue formed by removing the hydrogen atoms of all the hydroxyl groups of a polyhydric alcohol selected from the group consisting of pentaerythritol, sorbitol, mannitol, a glycoside, glycerol, and a polyglycerol represented by the following formula (4):

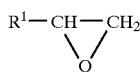

(4)

wherein a represents a number of 2–20, and an alkylene oxide adduct thereof.

11. The process of claim 8, wherein G in the general formula (1) is a residue formed by removing the hydrogen atoms of all the hydroxyl groups of a polyhydric alcohol selected from the group consisting of pentaerythritol, glycerol, and a polyglycerol represented by the following formula (5):

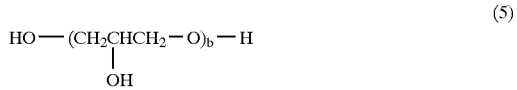

(5)

wherein b represents a number of 2–4.

12. The process of claim 8, wherein $R^{1a}$ is an alkyl group represented by the following formula (6) or (7):

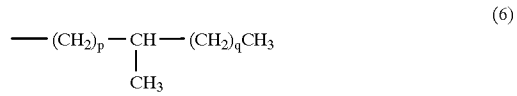

(6)

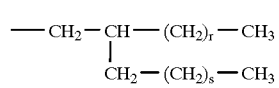

(7)

wherein p and q individually represent an integer of 0–33, with the proviso that the sum of p and q amounts to 13–33, and r and s individually represent an integer of 0–31, with the proviso that the sum of r and s amounts to 11–31.

13. The process of claim 8, wherein $R^{1a}$ is an oleyl group.

14. The process of claim 8, wherein $R^{1a}$ is a linear or branched alkyl group having 6–36 carbon atoms or a linear or branched alkenyl group having 6–36 carbon atoms.

15. A cosmetic composition, comprising a fatty acid ester of an etherified polyhydric alcohol represented by the following general formula (1):

wherein G reprsents a residue formed by removing the hydrogen atoms of all the hydroxyl groups of a polyhydric alcohol having at least three hydroxyl groups;

x groups A may be the same or differnt from one another and individually represent the following formula (2) or (3):

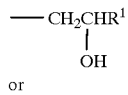

(2)

(3)

in which $R^1$ represents $R^{1a}$ or $-CH_2OR^{1a}$, wherein
$R^{1a}$ is a linear or branched alkyl group having 1–36 carbon atoms or a linear or branched alkenyl group having 1–36 carbon atoms, y groups B may be the same or different from one another and individually represent a hydrogen atom or a linear or branched alkanoyl group having 2–11 carbon atoms, with the proviso that at least one of y groups B is said linear or branched alkanoyl group having 2–11 carbon atoms; and x and y individually represent a number of 1 or greater, with the proviso that the sum of x and y amounts to the number of the hydroxyl groups of the polyhydric alcohol corresponding to G.

16. The cosmetic composition according to claim 15, wherein B in the general formula (1) is a hydrogen atom or a linear or branched alkanoyl group having 2–4 carbon atoms.

17. The cosmetic composition according to claim 15, wherein G in the general formula (1) is a residue formed by removing the hydrogen atoms of all the hydroxyl groups of a polyhydric alcohol selected from the group consisting of pentaerythritol, sorbitol, mannitol, a glycoside, glycerol, and a polyglycerol represented by the following formula (4):

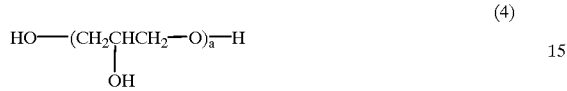

(4)

wherein a represents a number of 2–20, and an alkylene oxide adduct thereof.

18. The cosmetic composition according to claim 15, wherein G in the general formula (1) is a residue formed by removing the hydrogen atoms of all the hydroxyl groups of a polyhydric alcohol selected from the group consisting of pentaerythritol, glycerol and a polyglycerol represented by the following formula (5):

(5)

wherein b represents a number of 2–4.

19. The cosmetic composition according to claim 15, wherein $R^{1a}$ is an alkyl group represented by the following formula (6) or (7):

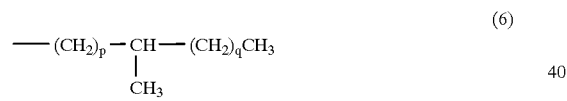

(6)

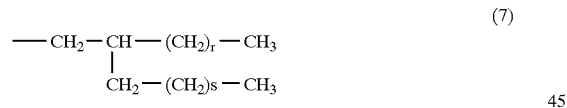

(7)

wherein p and q individually represent an integer of 0–33, with the proviso that the sum of p and q amounts to 13–33, and r and s individually represent an integer of 0–31, with the proviso that the sum of r and s amounts to 11–31.

20. The cosmetic composition according to claim 15, wherein $R^{1a}$ is an oleyl group.

21. The cosmetic composition according to claim 15, wherein $R^{1a}$ is a linear or branched alkyl group having 6–36 carbon atoms or a linear or branched alkenyl group having 6–36 carbon atoms.

22. A process for producing an etherified polyhydric alcohol represented by the following general formula (10):

$G(A)_xH_y$ (10)

wherein G represents a residue formed by removing the hydrogen atoms of all the hydroxyl groups of a polyhydric alcohol having at least three hydroxyl groups;
x groups A may be the same or different from one another and individually represent the following formula (2) or (3):

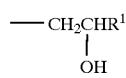

(2)

or

(3)

in which $R^1$ represents $R^{1a}$ or $—CH_2OR^{1a}$,
$R^{1a}$ is a linear or branched alkyl group having 1–36 carbon atoms or a linear or branched alkenyl group having 1–36 carbon atoms, x and y individually represent a number of 1 or greater, with the proviso that the sum of x and y amounts to the number of the hydroxyl groups of the polyhydric alcohol corresponding to G, which the process comprises reacting a fatty acid ester of a polyhydric alcohol represented by the following general formula (8):

$G(B)_z$ (8)

wherein G has the same meaning as defined above;
z groups B may be the same or different from one another and individually represent a hydrogen atom or a linear or branched alkanoyl group having 2–11 carbon atoms; and z represents the sum of x and y, with the proviso that z groups B contain at least one hydrogen atom and linear or branched alkanoyl group having 2–11 carbon atoms as a whole, with an epoxy compound represented by the following general formula (9):

(9)

wherein $R^1$ has the same meaning as defined above, thereby forming a fatty acid ester of an etherified polyhydric alcohol represented by the following general formula (1):

$G(A)_x(B)_y$ (1)

wherein G, A, B, x and y have the same meaning as defined above, with the proviso that y groups B may be the same or different from one another, and at least one of y groups B is the acyl group, and then hydrolyzing the fatty acid ester (1).

23. The process according to claim 22, wherein B in the general formulae (8) and (1) is a hydrogen atom or a linear or branched alkanoyl group having 2–4 carbon atoms.

24. The process according to claim 22, wherein G in the general formulae (8), (1) and (10) is a residue formed by removing the hydrogen atoms of all the hydroxyl groups of a polyhydric alcohol selected from the group consisting of pentaerythritol, sorbitol, mannitol, a glycoside, glycerol, and a polyglycerol represented by the following formula (4):

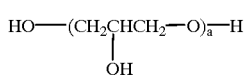 (4)

wherein a represents a number of 2–20, and an alkylene oxide adduct thereof.

25. The production process according to claim 22, wherein G in the general formulae (8), (1) and (10) is a residue formed by removing the hydrogen atoms of all the hydroxyl groups of a polyhydric alcohol selected from the group consisting of pentaerythritol, glycerol, and a polyglycerol represented by the following formula (5):

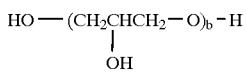 (5)

wherein b represents a number of 2–4.

26. The production process according to claim 22, wherein $R^{1a}$ is an alkyl group represented by the following formula (6) or (7):

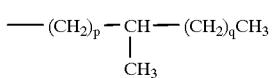 (6)

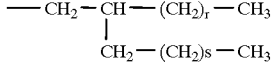 (7)

wherein p and q individually represent an integer of 0–33, with the proviso that the sum of p and q amounts to 13–33, and r and s individually represent an integer of 0–31, with the proviso that the sum of r and s amounts to 11–31.

27. The production process according to claim 22, wherein $R^{1a}$ is an oleyl group.

28. The production process according to claim 22, wherein $R^{1a}$ is a linear or branched alkyl group having 6–36 carbon atoms or a linear or branched alkenyl group having 6–36 carbon atoms.

* * * * *